United States Patent [19]

Sogi et al.

[11] 4,160,699

[45] Jul. 10, 1979

[54] DRIVE SYSTEM FOR AUTOMATIC CULTURE APPARATUS

[75] Inventors: Shinroku Sogi; Makoto Yoshinaga, both of Hachioji; Toshio Shinohara, Chofu; Takayuki Aihara; Ikuo Tawara, both of Hachioji, all of Japan

[73] Assignee: Olympus Optical Co., Ltd., Tokyo, Japan

[21] Appl. No.: 847,553

[22] Filed: Nov. 1, 1977

[30] Foreign Application Priority Data

Nov. 9, 1976 [JP] Japan ............................... 51-133695

[51] Int. Cl.² .............................................. C12K 1/10
[52] U.S. Cl. ..................................... 435/287; 414/292
[58] Field of Search ........ 195/127, 103.5 R, 103.5 M, 195/103.5 K, 139; 214/17 B

[56] References Cited

U.S. PATENT DOCUMENTS

| | | | |
|---|---|---|---|
| 3,728,227 | 4/1973 | Elson et al. | 195/127 |
| 3,853,711 | 12/1974 | Heden | 195/127 X |
| 3,874,525 | 4/1975 | Hassan et al. | 214/17 B |
| 4,030,622 | 6/1977 | Brooks et al. | 214/17 B |

*Primary Examiner*—Raymond N. Jones
*Assistant Examiner*—Robert J. Warden
*Attorney, Agent, or Firm*—Ostrolenk, Faber, Gerb & Soffen

[57] ABSTRACT

An automatic culture apparatus includes an airtight casing, a culture vessel platform, a culture observation platform and a separation/distribution work platform disposed in layered configuration with suitable vertical spacings between them. A drive system for the apparatus comprises an opening formed centrally in each of the platforms; a culture vessel carrier for conveying a culture vessel to each of the platforms through the openings; a transfer arm for loading and unloading a culture vessel on or from the carrier and any one of the platforms; a first drive mechanism for operating the carrier and the transfer arm; and a second drive mechanism for driving any one of the platforms. The second drive mechanism is mounted hermetically in the casing. By operating suitable drive mechanisms to actuate the various parts, a culture vessel may be automatically transferred and distributed on each of the platforms without causing contamination in a safe and efficient manner, for automatic growth of the medium being cultured under an optimum environment.

5 Claims, 7 Drawing Figures

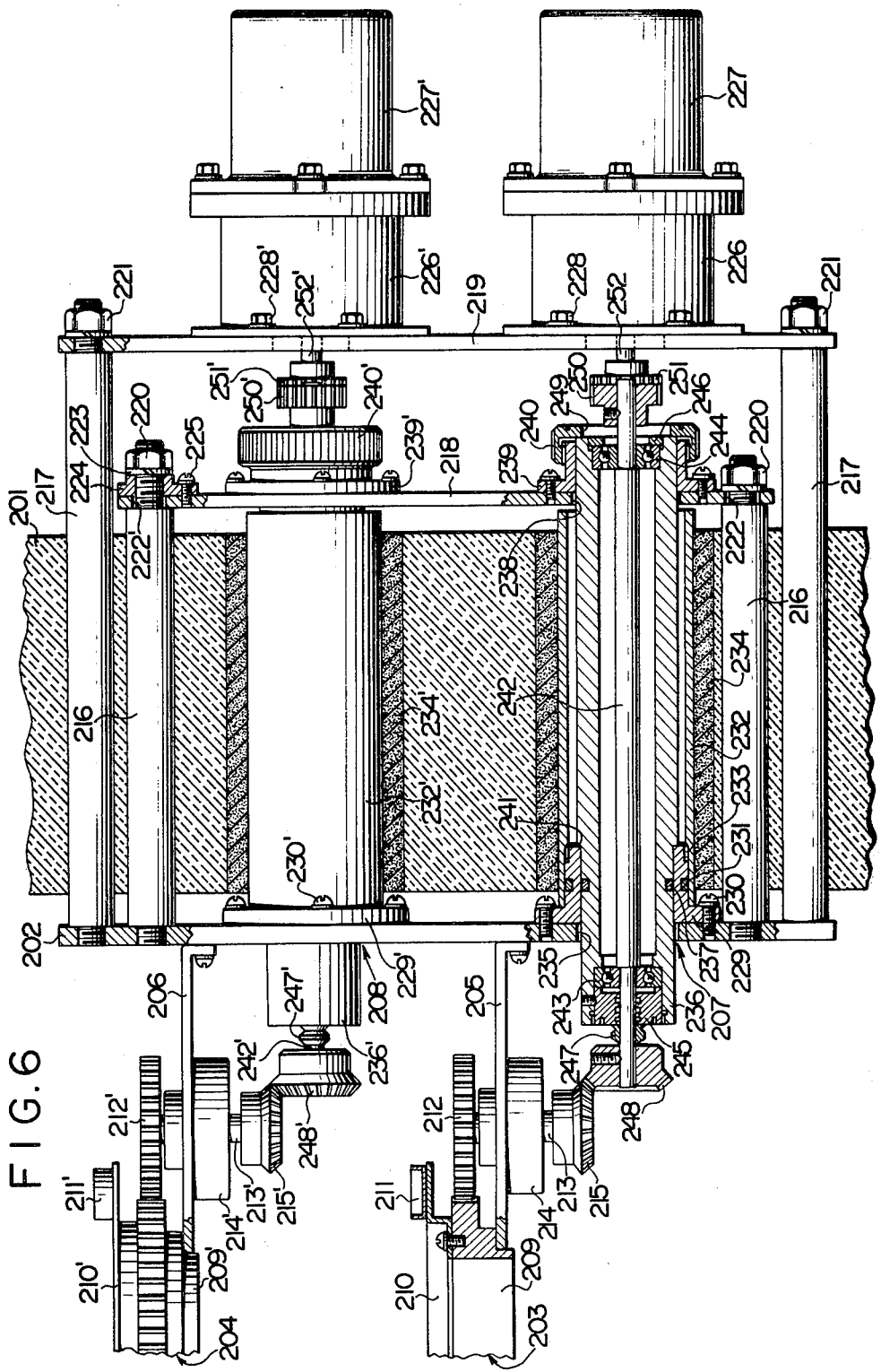

DRIVE SYSTEM FOR AUTOMATIC CULTURE APPARATUS

BACKGROUND OF THE INVENTION

The invention relates to a drive system for apparatus for automatic culture of biological tissues or cells.

The culture of biological tissues or cells is an essential experimental technique for conducting a microscopic investigation of such medium in every field including the medical science, biology, pharmacy and agricultural science. However, the culture of biological tissues or cells over successive generations involves technical difficulties, which have prevented a stabilized cultured strain from being obtained. However, with the recent development of gas culture in an incubator, namely, culturing in a particular gas atmosphere, the culture over successive generations of cells of special kinds such as liver, neuron, pituitary gland has been made possible through their culturing has been considered difficult in the prior art practice.

The culture over successive generations will be briefly summarized below. A given number of cells are diluted in a culture solution in the form of a suspension, which is injected into a culture vessel such as petri dish. The vessel is placed still in an incubator for culturing of the cells under given gas atmosphere and temperature environment. After a given period of time, the vessel is removed from the incubator and examined for the growth or the increase of the number of cells with the use of a microscope. When it is determined that the intended cells have grown to the full extent of the vessel, it is transferred to a strain-free clean bench, and the culture solution in the vessel is withdrawn with a pipette and disposed. Subsequently, a buffer solution is injected into the vessel to clean the remaining cells. The buffer solution used for the purpose of cleaning is again withdrawn and disposed. The grown cells which attach to the bottom of the vessel are freed therefrom by the injection of an enzyme such as trypsin. The freed cells are separated and collected by using a centrifuge. Thus, the freed cells are separated from the enzyme in the centrifuge, and the decantered solution or enzyme is withdrawn and disposed. The centrifuge may not be used for separating the cells from the enzyme depending on the variety of cells. In this instance, the enzyme is withdrawn and disposed immediately before the cells attaching to the bottom of the vessel are freed by means of the enzyme. Subsequently, a culture solution is injected for distributing the cells in a given diluted concentration, and the cells are again brought into suspension by means of a pipette. The solution containing the cells in suspension is then distributed into fresh culture vessels in given quantities. After such dilution and distribution operations, the vessels are removed from the clean bench and placed still in an incubator which maintains a given environment for allowing the culturing process to proceed.

The conventional technique described above suffers from a number of disadvantages. It will be seen that the examination of the growth of the tissues or cells under the microscope often requires the removal of the culture vessel out of the incubator and into the outer atmosphere. This may cause a sudden change in the culturing conditions such as the gas atmosphere, temperature, humidity or the like, causing a critical influence upon the tissues or cells being cultured. In addition, the exposure to the outer atmosphere may cause a contamination by miscellaneous strains. Thus, the examination brings forth the influence of a change in the environmental conditions and a more direct influence by mixture with miscellaneous strains.

The various operations required for culturing over successive generations rely on a manual operation by an operator in the clean bench. This means that any slight difference in the various operations may have a direct influence upon the culturing result of the tissues or cells. Since the experience and skill of the culturing technique varies from operator to operator, it is difficult to provide a standard procedure for the culturing technique. This makes it impossible to produce the tissues or cells being cultured which are of uniform quality. As a consequence, when different groups of researchers are conducting a common study on the same theme, their conclusions may differ from each other as a result of the difference in the tissues being cultured. In extreme cases, the conclusions may be opposite to each other. This means that the cells or tissues cultured with the conventional technique tended to lack the reliability.

It takes at least two years to train a skilled operator. As a result, there is a continued shortage of such operators, and researchers often have to perform the culturing operation themselves rather than exclusively directing their effort to their study.

In view of these considerations, the present invention is directed towards an automatic culture apparatus capable of performing the described culturing operations automatically in order to eliminate the contamination which may occur as a result of the exposure to the outer atmosphere. Such apparatus also serves to remove the influence of manual operations upon the cultured results and to permit a standard and uniform procedure for the various culturing operations. With this apparatus, the cells which are to be cultured over successive generations are diluted with a culture solution, and a given number of cells are distributed into separate culture vessels to be cultured while they remain at rest. It is necessary that the growth of cells can be observed under a microscope from time to time while the culture is being continued. When the growth has proceeded to a point that a given number of cells are produced, it is necessary to inject an enzyme solution into the vessel to free the cells attaching to the bottom thereof, followed by centrifuging and distributing them into fresh vessels. All of these operations must be automatically performed in a chamber in which a given environment is maintained. To this end, the automatic culture apparatus of the present invention is designed to permit the performance of the described operations and observation, by disposing the observing microscope, distributor and other mechanical devices within the chamber. Then it is necessary to provide a drive system to move a culture vessel containing the cells between various mechanisms or devices which are mounted within the chamber.

SUMMARY OF THE INVENTION

It is an object of the invention to provide a drive system for automatic culture apparatus.

With the present invention, all of the steps required for the culture process can be continuously performed without requiring the removal of the culture vessel from the apparatus, and hence preventing its exposure to the outer atmosphere to cause a change in the environment, thus eliminating all of the problems experienced in the prior art.

In the drive system of the invention, a motor used as a drive source is provided externally of the cell culturing chamber, and this advantageously eliminates adverse influences of the heat produced by the motor upon the culture apparatus in which a definite culturing environment must be closely maintained. A culture vessel carrier is detachably mounted on an interconnecting tube or carrier vertical movement shaft and with a transfer arm vertical movement tube through a dovetail key and dovetail groove arrangement, the use of which permits them to be disassembled in a simple manner, thereby facilitating their repair, cleaning and replacement.

The drive system includes another drive mechanism for performing various operations, and the majority of parts of which is positively sealed and disposed outside the particular atmosphere maintained within the envelope of the culture apparatus. This avoids an early damage to the drive motor which may be caused if it is disposed within the humidity of the atmosphere. In addition, the disassembly and assembly of drive components can be simply achieved when replacing the parts, and any leakage of the atmosphere after the re-assembly can be reliably prevented without requiring any particular attention during the assembling operation.

BRIEF DESCRIPTION OF THE DRAWINGS

FIG. 6 is a cross section taken along the line A—A shown in FIG. 5.

DESCRIPTION OF PREFERRED EMBODIMENT

Figure 1B:
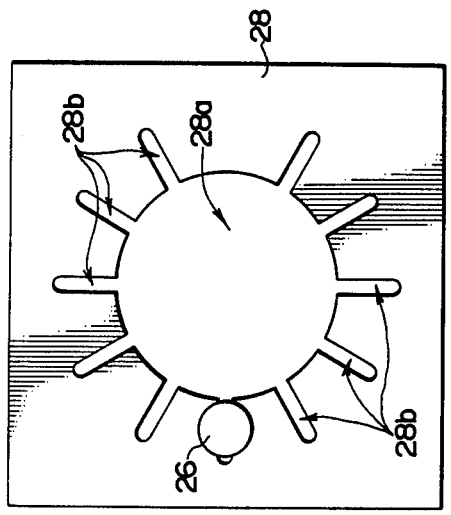
FIG. 1B is a schematic plan view of a culture vessel receptacle.
Figure 1A:
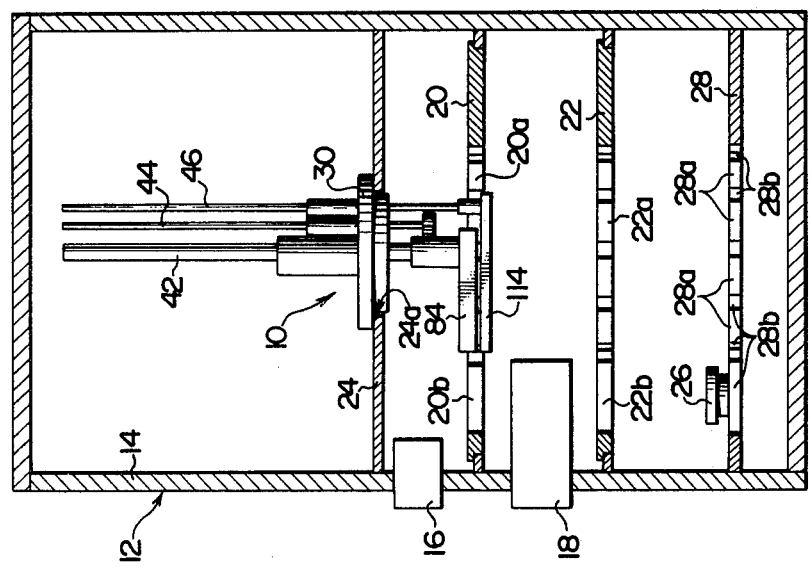
FIG. 1A is a schematic section of one exemplary form of automatic culture apparatus to which the invention may be applied.

Referring to FIG. 1A, an automatic culture apparatus in which the invention is applied is schematically shown. The automatic culture apparatus 12 includes an airtight casing or envelope 14 in the form of a closed container in which a particular gas and temperature environment is maintained.

Mounted on the sidewall of the casing 14 are a separation/distribution mechanism 16 for separating and distributing the cells being cultured, and an observation instrument 18, such as microscope, which is used to observe the growth of the cells. A separation/distribution work table or platform 20 and a culture observation platform 22 are rotatably mounted inside the casing 14 below the components 16 and 18, respectively. The drive system of the invention includes a vessel transfer unit 10 which is operably supported on a carrier support platform 24 which is secured to the casing above the platform 20. A vessel platform 28 is secured inside the casing 14 below the observation platform 22 and receives culture vessels 26 thereon. Culture vessels 26 contain the cells being cultured. As shown, the platform 20, the observation platform 22 and the vessel platform 28 are centrally formed with through-openings 20a, 22a and 28a, respectively, which are of the same diameter and which are formed with a plurality of radially extending slots 20b, 22b and 28b (see FIG. 1B) respectively. These slots have a width which permits a transfer arm of the carrier 10 to move thereinto as will be further described below. Culture vessels 26 are placed on the vessel platform 28 (only one being shown) in a manner to straddle across the slot 28b. It should be understood that while FIG. 1B only shows a reduced number of slots, an actual system will include approximately thirty-two such slots, each receiving a vessel thereon. When the separation/distribution, and/or the observation of the growth of the cells contained in a vessel 26 placed on the platform 28 is required, the vessel 26 is transferred from the platform 28 to an elevatable or vertically movable vessel carrier 84 of a transfer unit (described below) by means of a transfer arm 114 of the transfer unit and thereafter carried onto the platform 20 or the observation platform 22.

Figure 2:
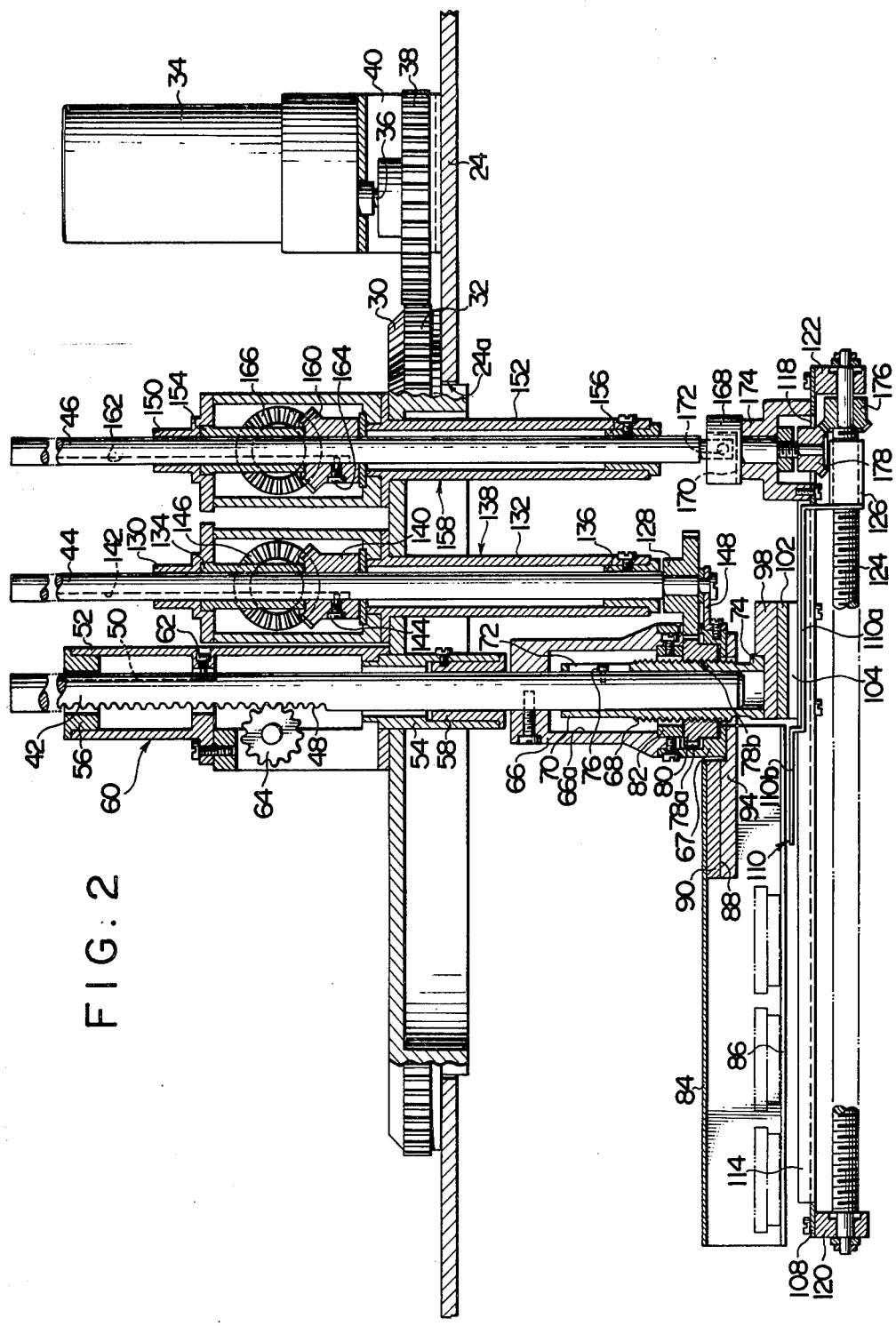
FIG. 2 is an elevational section of the drive system according to the invention, in particular, a drive mechanism associated with conveying of the vessel.

Referring to FIGS. 1 and 2, the transfer unit 10 comprises a rotatable disc 30 rotatably carried by the support platform 24. The disc 30 is a loose fit in a through-opening 24a which is centrally formed in the support 24 so as to permit it to rotate in a smooth manner. To permit a rotation of the disc 30, it is peripherally formed with gear teeth 32, which mesh with a gear 38 fixedly mounted on the rotary shaft 36 of a drive motor 34. The motor 34 is fixedly mounted on the support 24 in a vertical position, by means of a mounting member 40. Thus, as the motor 34 is set in motion, the disc 30 can be rotated smoothly relative to the support 24.

A plurality of vertically extending shafts 42, 44 and 46 extend through the disc 30 for causing a vertical movement of the vessel carrier, a vertical movement of the transfer arm and a horizontal movement of the transfer arm, respectively. In its upper region, the shaft 42 is formed with a rack 48 and also with a keyway 50 which is located diametrically opposite to the rack 48. The shaft 42 is guided for vertical movement by a guide mechanism 60 comprising a pair of sleeve support tubes 52, 54 fixedly mounted on the disc 30, and a pair of sleeves 56, 58 secured within the support tubes. The keyway 50 of the shaft 42 is engaged by one end of a key screw 62 which is threadably engaged with the sleeve support tube 52, thus preventing a rotation of the shaft 42 relative to the disc 30. The rack 48 meshes with a pinion 64 connected with a motor (not shown) which is fixedly mounted on the disc 30. In this manner, the rotation of the pinion 64 causes a vertical movement of the shaft 42.

Smoothly fitted on the lower portion of the shaft 42 is a transfer arm vertical movement tube 70 having a connection tube 66 which includes a hollow space 66a and having a cap 67 secured to the lower end thereof. The operating tube 70 is peripherally formed with threads 68 and extends through a central bore in the cap 67. In its top portion, the tube 70 is formed with an axially extending groove 72, and is also formed with a flange 74 at its lower end. A key screw 76 threadably engages the shaft 42 with its head projecting into the slot 72 to prevent a rotation of the tube 70 relative to the shaft 42, but permits it to move vertically in a smooth manner. Received within the cap 67 is a drive wheel 80 having gear teeth 78a on its outer periphery and having female threads 78b on its inner periphery, the drive wheel engaging the threads 68 on the tube 70. The drive wheel 80 is rotatable relative to the tube 70, but its vertical movement is prevented by a stop 82 which is secured to the connecting tube 66. As a consequence, when the nut 80 is rotated, the tube 70 smoothly moves in the vertical direction relative to the shaft 42.

Figure 3:
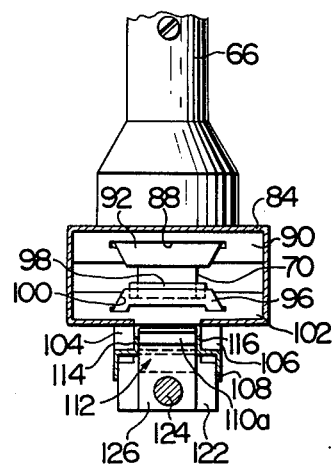
FIG. 3 is a cross section of the interconnecting tube, vessel carrier and connecting plate used in the drive mechanism of FIG. 2, illustrating their connection.

The connecting tube 66 has a horizontally extending vessel carrier 84 mounted thereon, which is utilized when transferring the culture vessel 26 between vessel platform 28, separation/distribution platform 20 and observation platform 22 and which temporarily receives the vessel during such transfer. The carrier 84 comprises a single sheet of metal which is folded into a rectangular configuration so as to form a channel 86 in its bottom which is of the same width as that of the slots 28b, 20b, 22b. The vessel carrier 84 includes a top panel, to the inside of which is secured a mounting member 90 having a dovetail groove 88 formed therein. Another mounting member 94, having dovetail key 92 (see FIG. 3) capable of engaging the groove 88, is secured to the lower end face of the cap 67. In this manner, the engagement of the dovetail key 92 on the mounting member 94 with the dovetail groove 88 in the mounting member 90 permits the vessel carrier 84 to be mounted on the connecting tube 66. Thus, the carrier 84 may be removed from the mounting member 94 when required.

A mounting member 98, having a dovetail key 96 formed thereon, is secured to the lower end of the tube 70, and the key 96 (see FIG. 3) is a tight fit in a dovetail groove 100 (see FIG. 3) formed in a connecting plate mounting member 102. As will be noted in FIG. 3, the mounting member 102 is formed with a pair of legs 104, 106 with a spacing therebetween which is substantially equal to the width of the channel 86 in the vessel carrier 84, and a connecting plate 108 is secured to the lower end faces of the legs 104, 106. The connecting plate 108 is formed with a groove 112 through which a transfer arm 110 (see FIG. 2) to be described later can extend, and also with a pair of upstanding pieces 114, 116 vertically depending from the opposite sides of the groove 112, with a through-opening 118 formed in its right-hand end region as shown in FIG. 2. Referring to FIG. 2, a pair of support members 120, 122 are secured to the opposite ends of the connecting plate 108, and rotatably support a threaded rod 124 which fixedly carries a pillar-shaped nut 126. Secured to one end of the nut 126 is the transfer arm 110 having a horizontally extending arm 110a and a vessel receiving portion 110b which extends horizontally beyond such horizontal arm 110a (see FIG. 2). The arm portion 110a of the transfer arm 110 is located between the upstanding pieces 114, 116 of the connecting plate 108 and is guided for reciprocating movement in one direction, by guide members (not shown). In this manner, a rotation of the nut 126 relative to the threaded rod 124 is blocked, and hence as the threaded rod 124 rotates, the nut 126 is caused to move horizontally along the threaded rod 124 together with the transfer arm 110. The mounting member 98 is secured to the tube 70 by fitting the connecting plate mounting member 102 in a manner such that the channel 86 in the vessel carrier 84 and the groove 112 in the connecting plate 108 extend horizontally and parallel to each other while maintaining their vertical alignment. Thus, when the drive wheel 80 is rotated to move the tube 70 upwardly relative to the shaft 42, the connecting plate 108 moves up, causing the vessel receiving portion 110b of the transfer arm 110 to extend through the channel 86 into the vessel carrier 84.

The drive wheel 80, which is used to cause a vertical movement of the tube 70, is driven for rotation by a gear 128 fixedly mounted on the lower end of the shaft 44 and which extends through a window in the cap 67 to mesh with the drive wheel 80. The shaft 44 is guided for vertical movement by a guide mechanism 138 comprising a pair of sleeve support tubes 130, 132 secured to and vertically depending from the disc 30, and a pair of sleeves 134, 136 secured inside the support tubes. A bevel gear 140 is rotatably fitted on the shaft 44 within the tube 130, and the shaft 44 and the gear 140 are slidable in the vertical direction but are caused to rotate integrally by engaging a key screw 144 fixedly mounted on the bevel gear 140 with a keyway 142 formed in the shaft 44. The lower end of the sleeve 134 prevents an upward movement of the bevel gear 140, which meshes with another bevel gear 146 disposed within the tube 130 and connected with a drive source, not shown. As will be seen from FIG. 2, the lower end of the shaft 44 is supported by a support plate 148 which is secured to the cap 67 integral with the connecting tube 66. As a consequence, as the bevel gear 146 rotates, an integral rotation is caused to the bevel gear 140, shaft 44 and gear 128 to cause a rotation of the drive wheel 80, which in turn causes a vertical movement of the tube 70. The shaft 44 is connected with the cap 67 of the connecting tube 66 through the support plate 148, so that they move integrally up and down as the shaft 42 moves vertically.

Figure 4:
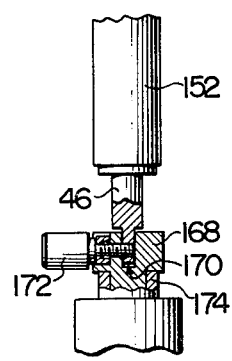
FIG. 4 is a side elevation, partly in section, of the transfer arm horizontal drive shaft and the support member for the connecting plate of the drive mechanism of FIG. 2, illustrating their connection.

The shaft 46 which is used to move the transfer arm in the horizontal direction, is guided for vertical movement by a guide mechanism 158 comprising a pair of sleeve support tubes 150, 152 secured to and depending vertically from the disc 30, and a pair of sleeves 154, 156 secured inside the support tubes. A bevel gear 160 is rotatably fitted on the shaft 46 within the tube 150, and both the shaft 46 and the gear 160 are caused to rotate integrally by the engagement of a key screw 164 on the gear 160 with a keyway 162 formed in the shaft 46. The lower end face of the sleeve 154 blocks an upward movement of the gear 160, which meshes with another bevel gear 166 disposed within the tube 150 and connected with a drive source, not shown. Referring to FIGS. 2 and 4, it will be noted that the lower end of the shaft 46 is flattened and is fitted into a groove 170 formed in the top of a rotating member 168 and locked thereto by a set screw 172. The groove 170 is formed in the top of the rotating member 168 to extend from the center toward and open into the periphery thereof. The rotating member 168 is rotatably supported by a support member 174 secured to the connecting plate 108 in a manner to cover the circular through-opening 118 therein. Hence, as the bevel gear 166 rotates, the bevel gear 160, shaft 46 and rotating member 168 rotate integrally, and as the shaft 42 moves vertically, the movement is transmitted through the connecting plate 108 to cause an integral movement of the shaft 46 in the vertical direction. A bevel gear 176 is fixedly mounted on the threaded rod 124 toward its right-hand end (see FIG. 2) and meshes with a bevel gear 178 which is fixedly mounted on the lower end of the shaft 46. Thus, rotation of the bevel gear 166 is transmitted through the bevel gear 160, shaft 46, rotating member 168, bevel gear 178 and bevel gear 176 to the threaded rod 124, thus moving the nut 126 and the transfer arm 110 in the horizontal direction.

Since the mounting member 98 and the connecting plate mounting member 102 are made integral by the engagement between the dovetail key and the dovetail groove, when the connecting plate mounting member 102 is withdrawn from the mounting member 98, with the set screw 172 which connects the lower end of the shaft 46 with the rotating member 168 removed, the connecting plate 108 can be removed from the shafts 42 and 46.

The operation of the transfer unit described above will now be explained.

The cells to be cultured are placed into a culture vessel 26 together with a culture solution, and the vessel 26 is placed on the vessel platform 28 of the apparatus 12 for culturing for a given period of time. In this instance, the vessel 26 is placed on the platform 28 so as to straddle across one of the slots 28b in the platform 28. When the cells contained in the vessel 26 have grown to a given degree, the grown cells are withdrawn from the vessel 26 by the separation/distribution mechanism, and is distributed into a plurality of separate, empty culture vessels 26 which are also placed on the platform 28 in order to permit a renewed culturing of the cells. By way of example, the operation of the transfer unit 10 will be described considering the observation which is needed to examine the growth of the cells of the first generation.

For the instance being considered, the shafts 42, 44, 46 and the connecting plate 108 assume their upper limit position shown in FIG. 2, and the nut 126 and its integral transfer arm 110 assume their rightmost position also shown in FIG. 2. In order to transfer the culture vessel 26 containing the cells being cultured from the vessel platform 28 to the culture vessel observation platform 22, the pinion 64 is initially rotated clockwise, as viewed in FIG. 2. The rotation of the pinion 64 lowers the shaft 42, and hence lowers the vessel carrier 84, shafts 44 and 46 and the connecting plate 108 therewith. The rotation of the pinion 64 is interrupted when the upper end of the channel 86 in the vessel carrier 84 coincides or becomes slightly lower than the top surface of the platform 28. The motor 34 is then set in motion to rotate the disc 30 until the channel 86 of the vessel carrier 84 moves into angular alignment with a particular one of the slots 28b in the platform 28 across which the vessel 26 to be transferred is located, whereupon the motor 34 is stopped. Subsequently, the bevel gear 166 is rotated to rotate the shaft 46 in a given direction, whereby such rotation is transmitted through the bevel gears 178, 176 to the threaded rod 124, thus moving the transfer arm 110 to the left from its rightmost position shown until the vessel receiving portion 110b thereof enters the slot 28b to a position below the vessel 26. Thereupon the rotation of the bevel gear 166 is interrupted, and the bevel gear 146 is rotated in a given direction. Such rotation is transmitted through the bevel gear 140 to the shaft 44 and is further transmitted through the gear 128 to the drive wheel 80, which in turn causes the tube 70 to move upward relative to the shaft 42, together with the connecting plate 108. This accompanies an upward movement of the transfer arm 110 which is associated with the connecting plate 108 through the threaded rod 124, thus causing its vessel receiving portion 110b to raise the particular vessel 26 from the upper surface of the platform 28. When the vessel 26 is slightly raised from the upper surface of the platform 28, the rotation of the bevel gear 146 is interrupted, and the bevel gear 166 is rotated in the opposite direction from that mentioned above, whereby the transfer arm 110 moves to the right, as viewed in FIG. 2, retracting the culture vessel 26 carried by the vessel receiving portion 110b from above the platform 28 into the vessel carrier 84. When the transfer arm 110 reaches a given position within the vessel carrier 84, the rotation of the bevel gear 166 is interrupted, and the bevel gear 146 is rotated in the opposite direction, whereby the transfer arm 110 moves down together with the connecting plate 108, completing the transfer of the particular vessel 26 from the platform 28 to the vessel carrier 84, with the vessel 26 initially located on the vessel receiving portion 110b of the transfer arm 110 placed straddling across the channel 86 in the carrier 84.

It should be understood that the rotation of the bevel gear 146 is interrupted when the vessel 26 on the transfer arm 110 is transferred onto the vessel carrier 84. Then the pinion 64 is rotated in the opposite direction from the direction initially mentioned to raise the vessel carrier 84 together with the connecting plate 108 until the lower surface of the vessel 26 transferred onto the vessel carrier 84 is substantially aligned with the culture observation platform 22, whereupon the rotation of the pinion is interrupted. If the channel 86 in the vessel carrier 84 is not aligned with the slot 22b in the observation level 22, the motor 34 may be energized to rotate the disc 30 through a suitable angle to achieve such alignment. Subsequently, the shaft 44 is rotated to move the transfer arm 110 upwardly in order to place the vessel 26 carried by the vessel carrier 84 onto the vessel receiving portion 110b of the transfer arm 110. The shaft 46 is thereafter rotated to move the transfer arm 110 to the left, as viewed in FIG. 2, and subsequently the shaft 44 is rotated to cause a downward movement of the transfer arm 110. Thereupon, the culture vessel 26, which was on the vessel carrier 84, is now transferred onto the observation platform 22. The above description covers the transfer of a single vessel 26 from the vessel platform 28 to the observation platform 22. It should be understood, however, that a plurality of vessels 26 placed on the platform 28 may be successively transferred onto the vessel carrier 84, which is then raised to the position of the observation platform 22 to transfer the plurality of vessels 26 onto the observation platform 22 in a sequential manner. When all of these steps are terminated, the carrier 84 and the transfer arm 110 are returned to their original position, namely, the uppermost position shown in FIG. 2.

From the above description which covers the transfer of the vessel 26 initially placed on the vessel platform 28 onto the observation platform 22, it will be appreciated by one skill in the art that the culture vessel 26 may be transferred from any one of the separation/distribution work platform 20, the culture observaton platform 22 and the culture vessel platform 28 to another one of them.

Figure 5:
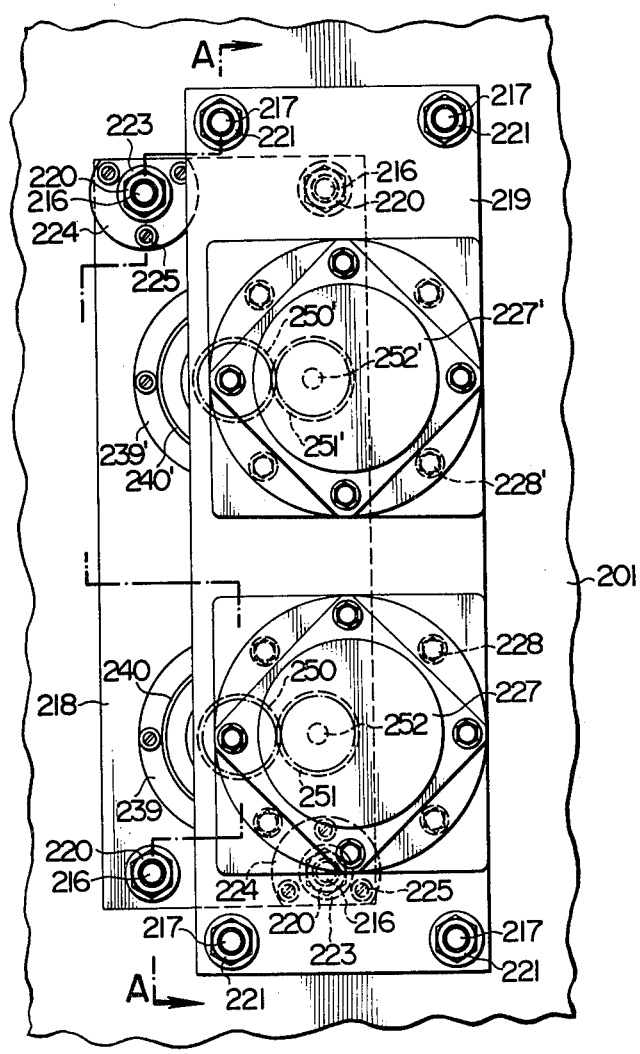
FIG. 5 is a side elevation of part of another drive mechanism associated with the separation/distribution work table and included in the drive system of the invention.

The drive system of the invention includes another drive mechanism associated with the separation/distribution work table. Referring to FIGS. 5 and 6, there is shown an environment isolation layer 201 which constitutes the outer wall of the culture apparatus 12. This corresponds to the casing or envelope 14 shown in FIG. 10A. A support plate 202 is secured to the inner sidewall of the isolation layer 201, and bearing plates 205, 206 or channels (not shown), which support these bearing plates, of an observation platform 203 and a separation/distribution work table 204 (corresponding to the observation platform 22 and the platform 20, respectively, shown in FIG. 1) are attached to the support plate 202. The observation platform 203 and the table 204 have a similar construction, and are associated with drive mechanisms 207, 208 which are of a similar construction. As a consequence, in the description to follow, only the drive mechanism 207 associated with the observation platform 203 will be explained, with parts of the table 204 and the drive mechanism 208 which correspond to those of the observation platform 203 and the drive mechanism 207 being designated by like reference characters with a prime "'".

The observation platform 203 comprises a rotatable platform 209 with external teeth which is rotatable on the bearing plate 205, and a circular vessel receiver 210 which is fixedly mounted on the platform 209. The receiver 210 is adapted to receive a plurality of culture vessels 211 along its periphery at equal intervals. The outer teeth of the platform 209 mesh with a gear 212 having a shaft 213 which is rotatably mounted on the plate 205 by means of a bearing 214, with the shaft 213 fixedly carrying a bevel gear 215.

In accordance with the invention, two sets of stanchions, each set comprising four stanchions 216, 217, are mounted on the support plate 202 by threadably engaging them therewith, these stanchions extending through the isolation layer 201 to the outside of the apparatus. A first mounting plate 218 is mounted on the free end of the stanchions 216, and a second mounting plate 219 is mounted on the free end of the stanchions 217. The stanchions 216 extend through the four corners of the first mounting plate 218 and are engaged by nuts 220, which may be clamped to fix the mounting plate on the outside of the casing of the culture apparatus. In the similar manner, the second mounting plate 219 is fixed to the casing. At its four corners, the first mounting plate 218 is formed with stanchion receiving holes 222, which are substantially greater than the diameter of the threaded free end of the stanchions 216. Two of the holes 222 are associated with sleeves 223 having a flange 224 through which a set screw 225 loosely extends and is threadably engaged with the first mounting plate 218. The sleeve 223 has a central bore which is sized to be a close fit with the threaded free end of the corresponding stanchion 216, thus permitting an adjustment of the position of the stanchion relative to the first mounting plate. In a similar manner, a drive motor 227 associated with a reduction gear box 226 is adjustably mounted on the second mounting plate 219 by means of bolts 228.

A boss 229 is mounted, by means of set screws 230, on the side of the support plate 202 which faces the environment isolation layer 201 so as to extend into the isolation layer 201. An outer pipe 232 having a threaded portion 233 is fixed to the outer periphery of the boss 229 with an O ring 231 interposed therebetween to provide a hermetic seal. The outer pipe 232 has a length extending through the environment isolation layer 201, with a silicone filler 234 packed between the pipe 232 and the layer 201 to provide a hermetic seal. The support plate 202 is formed with a through-opening 235 which is coaxial with the central bore of the boss 229, and an inner pipe 236 extends therethrough, an 0 ring 237 being provided between the inner pipe and the boss 229 to provide a hermetic seal. One end of the inner pipe 236 projects into the apparatus through the opening 235 while its other end extends through an opening 238 formed in the first mounting plate 218 and through a boss 239 which is fixedly mounted on the outside of the first mounting plate 218 in coaxial relationship with the opening 238.

A box nut 240 having a knurled periphery is threadably engaged with the outer periphery of the free end of the boss 239 to urge the inner pipe 236 to the left, as viewed in FIG. 6 causing a shoulder 241 formed in the outer periphery of the inner pipe 236 to abut against the boss 229 to fix the position of the inner pipe 236. A drive shaft 242 extends through the inner pipe 236 and is supported by a pair of bearings 243, 244 located at the opposite ends of the pipe 236. One of the bearings, 243, is locked against withdrawal by a ring 245 threadably engaging the corresponding end of the inner pipe 236 and which also provides a sealing function. The other bearing 244 is locked against withdrawal by a ring 246 which threadably engages the corresponding end of the inner pipe 236. The ring 245 has a bore which is sized so that the drive shaft 242 is a close fit therein, and a labyrinth packing is provided between the drive shaft 242 and the ring. In addition, a V-seal 247 is fitted over the drive shaft 242 to provide a seal between the ring 245 and the shaft 242.

A bevel gear 248 is fixedly mounted on the end of the drive shaft 242 which projects outside of the ring 245, and meshes with the bevel gear 215. A pinion 250 is fixedly mounted on the end of the drive shaft 242 which extends through the central opening 249 in the box nut 240, and meshes with a drive gear 251 which is fixedly mounted on the output shaft 252 of the reduction gear box 226.

In operation, the drive motor 227 may be repeatedly turned on and off. The rotation of the motor shaft is reduced in speed by the gear box 226 and is transmitted through the output shaft 252, drive gear 251, pinion 250, drive shaft 242, bevel gears 248, 215, shaft 213 and gear 212 to the observation level 203, thus stepwise rotating it through an angular increment corresponding to the pitch of the culture vessels 211 thereon. When it stays at rest between the incremental rotation, a particular vessel 211 thereon can be examined at home position.

In the assembled condition, although the drive mechanism has parts which extend through the environment isolation layer, the particular atmosphere or environment within the culture apparatus is completely isolated from the outer atmosphere by means of the silicone filler 254, O rings 231, 237, ring 245 and V-seal 246, thus positively preventing a leakage of the atmosphere.

When certain parts of the drive mechanism is to be replaced for reason of abrasion, the nuts 221 may be unscrewed to remove the second mounting plate 219 together with the reduction gear box 226, motor 227 and drive gear 251. Subsequently, the box nut 240 may be removed to withdraw the inner pipe 236 together with the drive shaft 242 extending therethrough while holding the gears 248, 250 fixedly mounted on its opposite ends, thus facilitating a replacement of the parts. After the parts are replaced, the assembly can be performed by a procedure which is opposite to the disassembly mentioned above. Thus, initially the inner pipe 236 is inserted into the outer pipe 232, together with the drive shaft 242 extending therethrough with the gears 248, 250 on its opposite ends, and the box nut 240 may be clamped. Subsequently, the nut 221 may be clamped to fix the second mounting plate 219 in position on the stanchions 217, thus completing the re-assembly.

In the example shown, whenever it becomes necessary to disassemble the first mounting plate 218, it can be reassembled in the original position by maintaining the position of the sleeves 223 relative thereto by means of the set screws 225, thus dispensing with the adjustment of the position relative to the support plate 202. The mounting of the drive motor 227 on a separate member, namely the second mounting plate 219, avoids the vibrations of the motor from being transmitted to the first mounting plate 218.

What is claimed is:

1. A drive system for an automatic culture apparatus of the type which includes an air tight housing having a culture vessel platform, a culture progress observation platform and a separation/distribution work platform disposed therein, said platforms being vertically displaced from each other, said drive system comprising:
    A) a through-opening centrally formed in each of said platforms;
    B) a culture vessel carrier movable between said platforms through said openings;
    C) a transfer arm for transferring a culture vessel between said vessel carrier and said vessel platform, said vessel carrier and said observation platform, and said vessel carrier and said work platform; and
    D) drive mechanism means for:
        (1) moving said vessel carrier and said transfer arm in the vertical direction such that said vessel carrier and said transfer arm may be moved between first, second and third positions adjacent said vessel platform, said observation platform and said work platform, respectively; and
        (2) moving said transfer arm in both the horizontal and vertical direction after said vessel carrier and transfer arm are placed in one of said first, second or third positions in such a manner that said transfer arm moves a culture vessel between said vessel carrier and the platform said transfer arm is adjacent.

2. A drive system according to claim 1, further including a second drive mechanism means for imparting rotation to at least one of said observation platform and said work platform.

3. A drive system according to claim 2, wherein said second drive means comprises:
    an outer pipe and an inner pipe extending through an environmental isolation layer which defines part of said air tight housing, said outer and inner pipes being mounted and fixed in position during use;
    means for forming an hermetic seal between said pipes and said isolation layer;
    a drive shaft extending through said inner pipe and rotatably supported thereby with an hermetic seal therebetween, one end of said drive shaft projecting into said air tight housing and being drivingly engaged with a rotatable platform which defines said at least one of said observation and said work platforms in such a manner that said at least one of said observation and said work platforms rotates responsive to rotation of said drive shaft; and
    a drive motor mounted on the outside of said air tight housing and drivingly engaged with the remaining end of said drive shaft whereby said drive shaft and said vessel receiving platform may be rotated by said drive motor.

4. A drive system according to claim 1, wherein said drive mechanism means comprises:
    a disk rotatably disposed in a compartment of said air tight housing, which compartment is vertically above said platforms;
    a first shaft coupled to said disc for rotation with said disc, said first shaft extendable vertically through said central openings;
    second and third shafts coupled to said disk both for rotation with said disk and for rotation about their own respective axis, said second and third shafts extendable vertically through said central openings;
    means coupling said first shaft to said vessel carrier and said transfer arm in such a manner that said vessel carrier and said transfer arm move together in the vertical direction responsive to movement of said first shaft in a vertical direction;
    means coupling said second shaft to said transfer arm in such a manner that said transfer arm moves in the vertical direction relative to said vessel carrier responsive to rotation of said second shaft about its own axis;
    means coupling said third shaft to said transfer arm such that said transfer arm moves in the horizontal direction responsive to rotation of said third shaft about its own axis;
    a first drive source for moving said first shaft in the vertical direction;
    a second drive source for rotating said second and third shafts; and
    a third drive source for rotating said disk.

5. A drive system according to claim 4, wherein said vessel carrier is detachably mounted on the distal end of said first shaft and said transfer arm is detachably mounted on the distal end of said third shaft.

* * * * *